United States Patent [19]

Grabowski et al.

[11] Patent Number: 5,684,040
[45] Date of Patent: Nov. 4, 1997

[54] COMPOSITIONS IN THE FORM OF SOLID SOLUTIONS

[75] Inventors: Sven Grabowski, Ludwigshafen; Winfried Mueller, Mannheim; Joerg Rosenberg, Ellerstadt; Rudolf Binder, Worms; Axel Sanner, Frankenthal, all of Germany

[73] Assignee: BASF Aktiengesellschaft, Ludwigshafen, Germany

[21] Appl. No.: 545,754

[22] PCT Filed: May 9, 1994

[86] PCT No.: PCT/EP94/01489

§ 371 Date: Nov. 7, 1995

§ 102(e) Date: Nov. 7, 1995

[87] PCT Pub. No.: WO94/26267

PCT Pub. Date: Nov. 24, 1994

[30] Foreign Application Priority Data

May 18, 1993 [DE] Germany .......................... 43 16 537.0

[51] Int. Cl.$^6$ .................................................. A61K 31/35
[52] U.S. Cl. .......................................................... 514/457
[58] Field of Search ...................................... 514/363, 457

[56] References Cited

U.S. PATENT DOCUMENTS 4,618,622 10/1986 Schlecker et al. ..................... 514/457
5,073,563 12/1991 Frickel et al. ......................... 514/365

FOREIGN PATENT DOCUMENTS 111 746 6/1984 European Pat. Off. .
38 30 355 3/1990 Germany .

OTHER PUBLICATIONS

Derwent Abstract, DE 830355 (1990).

*Primary Examiner*—Raymond Henley, III
*Attorney, Agent, or Firm*—Keil & Weinkauf

[57] ABSTRACT

Compositions in the form of solid solutions containing
a) 1–90% by weight of a coumarin derivative A from the group of alkoxycoumarins with a heterocyclic substituent or of hydroxycoumarins esterified with a sulfonic acid as active substance and
b) 10–99% by weight of at least one water-soluble polymer B as carrier substance.

9 Claims, No Drawings

COMPOSITIONS IN THE FORM OF SOLID SOLUTIONS

The present invention relates to novel compositions in the form of solid solutions, containing a) 1–90% by weight of a coumarin derivative A from the group of alkoxycoumarins with a heterocyclic substituent or of hydroxycoumarins esterified with a sulfonic acid as active substance and b) 10–99% by weight of at least one water-soluble polymer B as carrier substance.

The invention additionally relates to a process for the production of these compositions and to their use as drugs.

Compositions in which the active substance is present homogeneously dispersed in a water-soluble polymer are generally known in numerous embodiments. For example, EP-A 240 773, EP-A 462 066, EP 521 310 and Drug Development and Industrial Pharmacy, 6 (2) (1980) 137–160 describe compositions containing hydroxypropylmethylcellulose or polyvinylpyrrolidone as carrier substance.

Alkoxycoumarins with a heterocyclic substituent

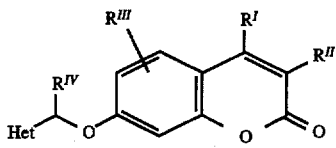

$R^I$, $R^{II}$, $R^{III}$, $R^{IV}$=substituents Het=N, S and O containing heterocyclic radical and sulfonic esters of hydroxycoumarins

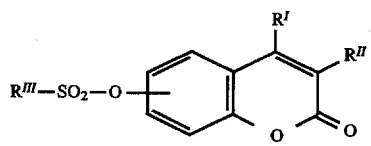

$R^I$, $R^{II}$, $R^{III}$=Substituents as well as pharmaceutical compositions containing these substances as active substances are known and are proposed in U.S. Pat. No. 5,073,563 for the treatment of disorders of the central nervous system, especially of neurodegenerative disorders and parkinsonism, and in EP-B 111 746 for the treatment of psychological disturbances, especially of depressions. The disadvantage of these active substances and their pharmaceutical compositions described therein is that they are unsatisfactory in respect of their bioavailability because of their low solubility in water. It is therefore possible for these coumarin derivatives which are in crystalline form to be absorbed only very slowly and incompletely after intake.

It is an object of the present invention to provide compositions in the form of solid solutions with good solubility and bioavailability as well as rapid absorption of the coumarin derivatives A.

We have found that this object is achieved by the compositions defined at the outset.

The invention furthermore relates to a process for their production, their use as drugs and their dosage forms.

The compositions according to the invention contain a) 1–90% by weight, preferably 10–40% by weight, of a coumarin derivative A from the group of alkoxycoumarins with a heterocyclic substituent or hydroxycoumarins esterified with a sulfonic acid as active substance and b) 10–99% by weight, preferably 60–90% by weight, of at least one water-soluble polymer B as carrier substance.

Suitable alkoxycoumarins A' with a heterocyclic substituent are the compounds specified in U.S. Pat. No. 5,073,563, and those which are preferably suitable here have a thiadiazole residue as heterocyclic substituent and are claimed in the cited publication. Particularly suitable are 4-Trifluoromethyl-7-(2-methyl-1,3,4-thiadiazol-5-yl) methoxycoumarin 3,4-Dimethyl-7-(2-isopropyl-1,3,4-thiadiazol-5-yl) methoxycoumarin 3,6-Dichloro-4-methyl-7-(2-cyclopropylthiazol-4-yl) methoxycoumarin 3,4-Dimethyl-7-(2-methylthiazol-4-yl)methoxycoumarin 3,4-Dimethyl-7-(2-phenylthiazol-4-yl)methoxycoumarin 3,4-Dimethyl-7-(2-benzylthiazol-4-yl)methoxycoumarin 3,4-Dimethyl-7-(2-isopropylthiazol-4-yl)methoxycoumarin 3,4-Dimethyl-7-(2-cyclopropylthiazol-4-yl) methoxycoumarin 3,6-Dichloro-4-methyl-7-(2-isopropylthiazol-4-yl) methoxycoumarin 6-Bromo-3-chloro-4-methyl-7-(2-isopropylthiazol-4-yl) methoxycoumarin Suitable hydroxycoumarins A" esterified with sulfonic acid are the compounds described in EP-B 111 746.

The principle according to the invention is very particularly suitable for compositions with 3,4-dimethyl-7-(2-isopropyl-1,3,4-thiadiazol-5-yl)methoxycoumarin A'/1

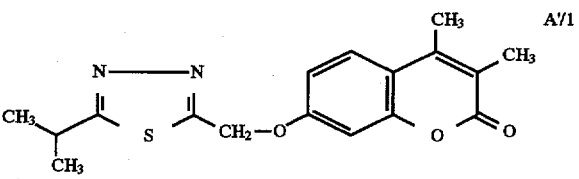

from the group of alkoxycoumarins A' with a heterocyclic substituent, and with 7-hydroxy-3,4-dimethylcoumarin ethanesulfonic ester A"/1

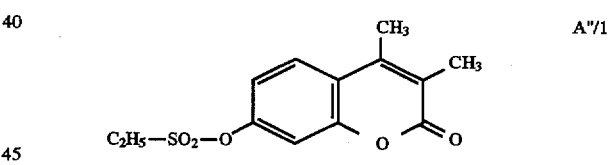

from the group of hydroxycoumarins A" esterified with sulfonic acid as active substance.

The following water-soluble polymers B may be mentioned:

alkylcelluloses such as methylcellulose hydroxyalkylcelluloses such as hydroxymethyl-, hydroxyethyl-, hydroxypropyl- and hydroxybutylcellulose hydroxyalkylalkylcelluloses such as hydroxyethylmethyl- and hydroxypropylmethylcellulose carboxyalkylcelluloses such as carboxymethylcelluloses alkali metal salts of carboxyalkylcelluloses such as sodium carboxymethylcellulose carboxyalkylcellulose esters N-vinylpyrrolidone/vinyl acetate copolymers polyvinylpyrrolidone polyvinyl alcohol polyacrylic acid and its salts polymethacrylic acid and its salts polyalkylene oxides such as polyethylene oxide and polypropylene oxide as well as copolymers of ethylene oxide and propylene oxide polysaccharides such as alginic acid, its alkali metal and ammonium salts, carrageenans, galactomannans, tragacanth, agar-agar, gum arabic, guar gum and xanthan gum
chitin derivatives such as chitosan
pectins such as sodium carboxymethylamylpectin
starches
and mixtures of these water-soluble polymers.

Preferred polymers B are methylcelluloses, hydroxypropylmethylcelluloses, hydroxypropylcellulose, polyvinylpyrrolidone and N-vinylpyrrolidone/vinyl acetate copolymers, especially polyvinylpyrrolidone and copolymers of 40–70% by weight of N-vinylpyrrolidone and 30–60% by weight of vinyl acetate.

The term water-soluble means that at least 0.5 g, preferably 2 g, of the polymer dissolve, possibly colloidally or with gel formation, in 100 g of water at 20° C.

A solid solution is present when the active substance is essentially in the form of a molecular dispersion in the polymer matrix (J. Pharm. Sci. 60 (1971) 1281–1302).

The compositions according to the invention can be produced by either melting the coumarin derivative A directly in the form of a physical mixture with the polymer B or mixing it with the polymer melt which has already been prepared.

Otherwise, mixing of the coumarin derivative A with the melt takes place in a conventional manner in extruders, preferably in single or twin screw extruders at a temperature in the range from 50° to 200° C. The shaping of the polymer melt which contains the coumarin derivative A to give the compositions according to the invention can take place, for example, by calendering the extrudate by the method described in EP-A 240 906 and by the processing method disclosed in DE-A 38 30 355 by comminuting the extrudate with rotating knives to pieces which are of equal volume and have a solidified surface but are still deformable and subsequently compressing to tablets in conventional tabletting machines.

The mixing of the active substance with the melt can also be carried out in other equipment suitable for this purpose and conventionally used to process plastics, e.g. calenders and injection molds.

The compositions according to the invention can also be produced by mixing the coumarin derivative A dissolved in a volatile solvent with the polymer melt. It is furthermore possible to obtain a mixture of coumarin derivative A and polymer B by dissolving them together in a volatile solvent and subsequently evaporating off the solvent. The cooled residue is further processed to solid dosage forms with shaping in conventional equipment as for the melt.

In some cases it may be expedient for the shaping to be preceded by application of the mixture of A and B, both in the form of the melt and in the form of a solution, for example onto a finely divided porous carrier material such as silica gel, and by formation of inclusion compounds e.g. with cyclodextrins and their derivatives.

It is additionally possible for the compositions according to the invention to contain conventional pharmaceutical ancillary substances such as fillers, lubricants, release agents, flow regulators, plasticizers, dyes and stabilizers in amounts of up to about 60% by weight. These amounts and others indicated hereinafter are in each case based on the total weight of the composition (=100%).

Examples of fillers which may be mentioned are the oxides of magnesium, aluminum, silicon and titanium as well lactose, mannitol, sorbitol, xylitol, pentaerythritol and its derivatives, with the amount of filler being about 0.02–50, preferably 0.2–20% by weight.

Examples of flow regulators which may be mentioned are the mono-, di- and triglycerides of long-chain fatty acids such as $C_{12}$-, $C_{14}$-, $C_{16}$- and $C_{18}$-fatty acid, waxes such as carnauba wax and the lecithins, with the amount being about 0.1–30, preferably 0.1–5, % by weight.

Examples of plasticizers which may be mentioned besides low molecular weight polyalkylene oxides such as polyethylene glycol, polypropylene glycol and polyethylene/propylene glycol are polyhydric alcohols such as propylene glycol, glycerol, pentaerythritol and sorbitol as well as sodium diethyl sulfosuccinate, the mono-, di- and triacetate of glycerol and polyethylene glycol stearate. The amount of plasticizer is moreover about 0.5–15, preferably 0.5–5% by weight.

Examples of lubricants which may be mentioned are stearates of aluminum or calcium as well as talc and silicones, with the amount thereof being about 0.1–5, preferably 0.1–3% by weight.

Examples of stabilizers which may be mentioned are light stabilizers, antioxidants, radical scavengers and stabilizers against microbial attack, the amount thereof preferably being about 0.01–0.05% by weight.

It is possible to mix the ancillary substances into the melt or solution of coumarin derivative A and polymer B. It is furthermore possible for the ancillary substances to be incorporated together with the coumarin derivative A into the polymer melt or into the solution of polymer B. In addition, mixtures of ancillary substances, the coumarin derivative A and the polymer B can be directly melted or dissolved together in a solvent. It is generally customary to melt a physical mixture of ancillary substances, coumarin derivative A and polymer B together.

The compositions according to the invention are used as drugs and employed in the form of powders, granules, tablets, pellets, suppositories or in capsules or in injection solution.

For oral administration it is advisable to provide the compositions with colored coatings, e.g. composed of titanium dioxide and of colored pigments, to improve the appearance. Suitable for improving the taste are coatings, for example glucose, sucrose, xylitol and mannitol.

The novel compositions in the form of solid solutions have advantages compared with the prior art in that the release of the coumarin derivative A is better, with the result that its bioavailability and absorption are considerably increased. The virtually homogeneous distribution of the amorphous coumarin derivative A in the polymeric carrier substance B results in an improvement in the solubility compared with crystalline coumarin derivative A.

EXAMPLES 1 to 9

The active substances used to produce the compositions according to the invention were
A'/1 3,4-dimethyl-7-(2-isopropyl-1,3,4-thiadiazol-5-yl)-methoxycoumarin and
A"/1 7-hydroxy-3,4-dimethylcoumarin ethanesulfonic ester.

They were synthesized by the methods described in U.S. Pat. No. 5,073,563 and EP-B 111 746 respectively.

The following commercially obtainable polymers B were used: (relative viscosity determined by the ASTM D 2365-72 capillary method (European Pharmacopoeia, vol. III, page 37))
B/1 copolymer of 60% by weight of N-vinylpyrrolidone (NVP) and 40% by weight of vinyl acetate; V=1.18–1.31 cps (1% solution in water, 25° C.) (Kollidon® VA64 from BASF AG)
B/2 Polyvinylpyrrolidone; V=1,430–1,585 cps (5% solution in water, 25° C.) (Kollidon® 17PF from BASF AG)

B/3 Polyvinylpyrrolidone; V=1.201–1.276 cps (1% solution in water, 25° C.) (Kollidon® 30 from BASF AG) (V=viscosity)

The following substances were used as ancillary substances C:

C/1 Polyethylene oxide, $\overline{M}_w$=6000 (Lutrol® E6000 from BASF AG)
C/2 Polyethylene oxide, $\overline{M}_w$=1500 (Lutrol® E1500 from BASF AG)
C/3 Lactose monohydrate, finely powdered; complying with DAB, Ph Eur, BP, USP (from Meggle)
($\overline{M}_w$=weight average molecular weight)

$AUC_x$=area under the curve with any particular administration $AUC_{i.v.}$=area under the curve on intravenous administration The in vivo test method entailed 1 tablet containing 300 mg of active substance being administered once to each dog (Beagle). Blood samples were taken at defined intervals for a period of 24 hours, and the concentration of the active substance in the blood was determined.

Details of these tests and the results are to be found in Table 1.

TABLE 1

| Example | Coumarin derivative A % by weight | | Polymer B % by weight | | Ancillary substance C % by weight | | Release of active substance after 1 h** (%) | absolute bioavailability F (%) |
|---|---|---|---|---|---|---|---|---|
| 1 | 20 | A"/1 | 80 | B/1 | — | | 6 | |
| 2 | 20 | A"/1 | 80 | B/2 | — | | 77 | |
| 3 | 20 | A"/1 | 60 | B/1 | 20 | C/1 | 37 | not investigated |
| 4 | 20 | A"/2 | 60 | B/2 | 20 | C/3 | 78 | |
| 5 | 19.5 | A"/1 | 40.5 | B/1 | 40 | C/3 | 22 | |
| 6 | 20 | A"/1 | 40 | B/2 | 40 | C/3 | 44 | |
| 7 (a)* | 50 | A'/1 | — | | 50 | C/3 | — | 1.00 (c) |
| 8 (b)* | 10 | A'/1 | — | | 90 | C/2 | — | 0.17 (d) |
| 9 | 10 | A'/1 | 90 | B/1 | — | | — | 3.05 (d) |

(a) Trituration of A'/1 with lactose
(b) Melt embedding
(c) F determined on one dog
(d) Average of F determined on 4 dogs (calculated from the median)
*Comparative example
**All forms reach 100% release of active substance after 8 h.

The amounts of coumarin derivative A, of polymer B and, in some cases, of ancillary substance C indicated in Examples 1 to 6 and 9 were mixed and then introduced into a twin screw extruder and extruded through 5 temperature zones from 60° to 130° C. The emerging polymer extrudate was fed into a calender mutually opposite concave depressions in the roller shells and was shaped to 1000 mg tablets. Transparent yellow tablets were obtained.

In Examples 1 to 6 release of active substance was measured by the USP XXI paddle method. This in vitro test method is used to determine the rate of dissolution of shaped articles containing active substance (e.g. tablets).

To do this, 900 ml of 0.1N hydrochloric acid containing 0.05 mol/l sodium lauryl sulfate were equilibrated at 37° C. in a 1 l round-bottom vessel. During the test the 1000 mg tablet to be tested was located in the center of the round bottom of the vessel below the paddle which rotated at 100 rpm. After the test had lasted 1 hour in each case, the amount of released active substance was determined by UV spectroscopy.

The absolute bioavailability F was determined in Examples 7 to 9 by means of an in vivo test method.

The bioavailability (biological availability; F) of a drug means the rate at which and the extent to which a therapeutically active constituent is released from a drug form, is absorbed and is finally available at the site of action. The bioavailability on intravenous administration is 100%.

The absolute bioavailability F is calculated using the following equation:

$$F = \frac{AUC_x \cdot \text{i.v. dose}}{AUX_{i.v.} \cdot \text{dose}_x} \cdot 100\%$$

AUC=area under the curve; area under the concentration-time plot (plasma level plot)

EXAMPLE 10

In another example, the bioavailability of A"/1 in the compositions according to the invention was measured. To do this, the pharmacokinetics of an extrudate composition (solid solution, active substance in amorphous form) were tested on dog (beagle). The plasma levels achieved are indicated in Table 2. For comparison, the values reached with granules (active substance in ground but crystalline form) were also determined.

Composition of extrudate (tablet, about 1 g):

| | |
|---|---|
| A"/1 | 18.87% by weight |
| Vinylpyrrolidone/vinyl acetate copolymer (60:40), (Kollidon® VA-64) | 41.13% by weight |
| Lactose | 40.00% by weight |

Composition of granules (capsules, size 0):

| | |
|---|---|
| A"1 | 77.55% by weight |
| Lactose | 11.64% by weight |
| Microcrystalline cellulose | 7.75% by weight |
| Polyvinylpyrrolidone, K value 30 | 2.58% by weight |
| Mg stearate | 0.48% by weight |

The results are to be found in Table 2.

TABLE 2

Plasma levels of A"/1 (esuprone) in Beagle dogs -
400 mg/kg of body weight of esuprone orally per day for 14 days

|  | Time after administration [h] | Animal No. 3 400 mg/kg Granules [ng/ml] | Animal No. 4 400 mg/kg Granules [ng/ml] | Animal No. 5 400 mg/kg Extrudate [ng/ml] | Animal No. 6 400 mg/kg Extrudate [ng/ml] |
|---|---|---|---|---|---|
| 1st administration | before substance administration | *) | 2.68 | 11.38 | 1.73 |
|  | 1 | 28.56 | 1.72 | 1245.92 | 2558.33 |
|  | 2 | 10.64 | 2.88 | 6907.77 | 8097.63 |
|  | 3 | 11.52 | 2.62 | 7307.85 | 12625.00 |
|  | 4 | 7.81 | 1.81 | 4653.01 | 5178.90 |
|  | 6 | 4.18 | 1.14 | 1011.11 | 1497.21 |
|  | 8 | 2.70 | 0.78 | 339.09 | 776.71 |
|  | 24 | 9.17 | 3.29 | 14.13 | 53.98 |
| 13th administration | 24 | 7.16 | 9.31 | 17.87 | 54.34 |
| 14th administration | 1 | 6.76 | 9.97 | 178.59 | 4795.10 |
|  | 2 | 16.48 | 0.66 | 263.98 | 12257.10 |
|  | 3 | 7.45 | 9.42 | 461.53 | 6466.05 |
|  | 4 | 4.70 | 7.15 | 542.59 | 3096.27 |
|  | 6 | 5.22 | 6.66 | 3503.58 | 1086.55 |
|  | 8 | 7.56 | 5.99 | 1242.95 | 714.03 |
|  | 24 | 1.63 | 3.33 | 7.48 | 36.62 |

*) Value below the detection limit of 0.2 [ng/ml]

We claim:

1. A solid oral dosable composition in the form of a solid solution containing
   a) 1–90% by weight of a coumarin derivative A from the group of alkoxycoumarins with a heterocyclic substituent or of hydroxycoumarins esterified with a sulfonic acid as active substance and
   b) 10–99% by weight of at least one water-soluble polymer B as carrier substance.

2. A composition as defined in claim 1, containing
   a) 10–40% by weight of the coumarin derivative A and
   b) 60–90% by weight of the water-soluble polymer(s) B.

3. A composition as defined in claim 1, containing 3,4-dimethyl-7-(2-isopropyl-1,3,4-thiadiazol-5-yl)methoxycoumarin or 7-hydroxy-3,4-dimethylcoumarin ethanesulfonic ester as coumarin derivative A.

4. A composition as defined in claim 1, containing polyvinylpyrrolidone and/or N-vinylpyrrolidone/vinyl acetate copolymers as polymer B.

5. A drug comprising a composition as defined in claim 1 in the form of powders, granules, tablets and pellets.

6. A composition as defined in claim 2, containing 3,4-dimethyl-7-(2-isopropyl-1,3,4-thiadiazol-5-yl)methyoxycoumarin or 7-hydroxy-3,4-dimethylcoumarin ethanesulfonic ester as coumarin derivative A.

7. A composition as defined in claim 2, containing polyvinylpyrrolidone and/or N-vinylpyrrolidone/vinyl acetate copolymers as polymer B.

8. A composition as defined in claim 3, containing polyvinylpyrrolidone and/or N-vinylpyrrolidone/vinyl acetate copolymers as polymer B.

9. A process for producing a composition as defined in claim 1, which comprises mixing the coumarin derivative A with polymer B in a solvent, removing the solvent, and further processing the melt or the residue remaining with shaping to particles.

* * * * *